(12) United States Patent
Sumi et al.

(10) Patent No.: US 11,918,372 B2
(45) Date of Patent: Mar. 5, 2024

(54) COGNITIVE FUNCTION EVALUATION SYSTEM, METHOD, AND STORAGE MEDIUM FOR DEMENTIA BY ANALYZING VOICE OF EVALUATEE FOR RECOGNITION, REMEMBERING OR JUGMENT CAPABILITIES

(71) Applicant: Panasonic Intellectual Property Management Co., Ltd., Osaka (JP)

(72) Inventors: Sadayuki Sumi, Hyogo (JP); Ryosuke Nagumo, Osaka (JP); Kengo Abe, Nara (JP); Yoshihiro Matsumura, Osaka (JP); Takashi Nishiyama, Hyogo (JP); Hirobumi Nakajima, Kyoto (JP); Kohji Sasabe, Osaka (JP); Makoto Kariyasu, Kyoto (JP); Takako Yoshimura, Hyogo (JP); Minoru Toyama, Oita (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 648 days.

(21) Appl. No.: 16/759,573

(22) PCT Filed: Oct. 15, 2018

(86) PCT No.: PCT/JP2018/038346
§ 371 (c)(1),
(2) Date: Apr. 27, 2020

(87) PCT Pub. No.: WO2019/087758
PCT Pub. Date: May 9, 2019

(65) Prior Publication Data
US 2021/0177340 A1 Jun. 17, 2021

(30) Foreign Application Priority Data
Nov. 2, 2017 (JP) .................................. 2017-213157

(51) Int. Cl.
*A61B 5/00* (2006.01)

(52) U.S. Cl.
CPC .......... *A61B 5/4803* (2013.01); *A61B 5/4088* (2013.01); *A61B 5/72* (2013.01)

(58) Field of Classification Search
CPC ....... A61B 5/4803; A61B 5/4088; A61B 5/72; A61B 5/4064; A61B 5/4842;
(Continued)

(56) References Cited

U.S. PATENT DOCUMENTS

| 2003/0069728 A1 | 4/2003 | Tato |
| 2008/0132768 A1 | 6/2008 | Shiomi |

(Continued)

FOREIGN PATENT DOCUMENTS

| JP | 6-297888 A | 11/1993 |
| JP | 2001-184509 A | 7/2001 |

(Continued)

OTHER PUBLICATIONS

Khodabakhsh et al (Analysis of speech-based measures for detecting and monitoring Alzheimer's disease, 2015.*

(Continued)

*Primary Examiner* — Serkan Akar
(74) *Attorney, Agent, or Firm* — Renner, Otto, Boisselle & Sklar, LLP

(57) ABSTRACT

A cognitive function evaluation device includes: an obtainment unit that obtains utterance data indicating a voice of an evaluatee uttering a sentence as instructed; a calculation unit that calculates, from the utterance data obtained by the obtainment unit, a feature based on the utterance data; an evaluation unit that compares the feature calculated by the calculation unit to reference data indicating a relationship between voice data indicating a voice of a person and a cognitive function of the person to evaluate the cognitive (Continued)

function of the evaluatee; and an output unit that outputs the sentence to be uttered by the evaluatee and outputs a result of evaluation by the evaluation unit.

13 Claims, 9 Drawing Sheets

(58) Field of Classification Search
CPC ... A61B 5/7275; A61B 5/749; A61B 2503/08; A61B 2562/0204; A61B 10/00; G10L 25/15; G10L 25/66
See application file for complete search history.

(56) References Cited

U.S. PATENT DOCUMENTS

| | | | |
|---|---|---|---|
| 2014/0107494 A1 | 4/2014 | Kato | |
| 2015/0118661 A1* | 4/2015 | Haruta | G16H 50/20 434/156 |
| 2018/0184964 A1* | 7/2018 | Simon | A61B 5/162 |

FOREIGN PATENT DOCUMENTS

| | | |
|---|---|---|
| JP | 2003-162294 A | 6/2003 |
| JP | 2004-240394 A | 8/2004 |
| JP | 2006-122375 A | 5/2006 |
| JP | 2006-230446 A | 9/2006 |
| JP | 2009-89800 A | 4/2009 |
| JP | 2011-255106 A | 12/2011 |
| JP | 2017-148431 A | 8/2017 |
| WO | 2005/104950 A1 | 11/2005 |
| WO | 2012/165602 A1 | 12/2012 |

OTHER PUBLICATIONS

Sapir et al (Formant Centralization Ratio (FCR): A proposal for a new acoustic measure of dysarthric speech, J Speech Lang Hear Res. Feb. 2010; 53(1): 114).*

International Search Report (ISR) and Written Opinion dated Nov. 27, 2018 in International (PCT) Application No. PCT/JP2018/038346.

Shimon Sapir, et al., "Voice, Speech, and Swallowing Disorders", Handbook of Parkinson's Disease, Fourth Edition, pp. 451-455 (date unknown).

Wolfram Ziegler, et al., "Speech timing in ataxic disorders: sentence production and rapid repetitive articulation", Neurology, vol. 47, Issue 1, Jul. 1996, pp. 208-214.

Strinzel, M. et al., "Acoustic and Perceptual Correlates of Vowel Articulation in Parkinson's Disease With and Without Mild Cognitive Impairment: A Pilot Study", Speech and Computer, 19th International Conference, SPECOM 2017 Aug. 13, 2017, pp. 56-60.

Chinese Office Action for corresponding Chinese Patent Application No. 201880070418.6 dated Sep. 5, 2022.

Chinese Search Report for corresponding Chinese Patent Application No. 201880070418.6 with English translation.

* cited by examiner

|  | NORMAL CONTROLS (NC) | MILD COGNITIVE IMPAIRMENT (MCI) | ALZHEIMER'S DISEASE (AD) |
|---|---|---|---|
| NUMBER OF SUBJECTS | 90 | 94 | 93 |
| AVERAGE MoCA SCORE | 27.4 | 22.1 | 16.2 |
| MoCA SCORE RANGE | 25.2–29.6 | 19.0–25.2 | 11.4–21.0 |

COGNITIVE FUNCTION EVALUATION SYSTEM, METHOD, AND STORAGE MEDIUM FOR DEMENTIA BY ANALYZING VOICE OF EVALUATEE FOR RECOGNITION, REMEMBERING OR JUGMENT CAPABILITIES

TECHNICAL FIELD

The present disclosure relates to a cognitive function evaluation device, a cognitive function evaluation system, a cognitive function evaluation method, and a storage medium.

BACKGROUND ART

Typical tests for evaluating cognitive functions include the Hasegawa dementia scale-revised (HDS-R), the mini-mental state examination (MMSE), and the clinical dementia rating (CDR) that cause evaluatees being suspected patients, whose cognitive functions are to be evaluated, to answer questions on test papers. These methods are used for evaluatees in medical institutions by doctors, clinical psychologists, or other practitioners trained to some extent.

Such an evaluation method using test papers requires a long test time, that is, a burden on evaluatees. Repeatedly taking the same test, evaluatees may remember the answers. To solve these problems, disclosed is a technique that a doctor or any other practitioner records the voice of an evaluatee answering questions in a test and analyzes the voice of the evaluatee (see, e.g., Patent Literature (PTL) 1).

CITATION LIST

Patent Literature

PTL 1: International Publication No. WO2012/165602

SUMMARY OF THE INVENTION

Technical Problem

There is a demand for simple and accurate evaluation on the cognitive function of an evaluatee.

To meet the demand, it is an objective of the present disclosure to provide a cognitive function evaluation device, for example, capable of simply and accurately evaluating the cognitive function of an evaluatee.

Solutions to Problem

A cognitive function evaluation device according to an aspect of the present disclosure includes: an obtainment unit configured to obtain utterance data indicating a voice of an evaluatee uttering a sentence as instructed; a calculation unit configured to calculate, from the utterance data obtained by the obtainment unit, a feature based on the utterance data; an evaluation unit configured to compare the feature calculated by the calculation unit to reference data indicating a relationship between voice data indicating a voice of a person and a cognitive function of the person to evaluate the cognitive function of the evaluatee; and an output unit configured to output the sentence to be uttered by the evaluatee and output a result of the evaluation by the evaluation unit.

A cognitive function evaluation system according to an aspect of the present disclosure includes: the cognitive function evaluation device; a voice collection device that detects the voice of the evaluatee; and a display device that displays the sentence and the result of the evaluation output by the output unit.

A cognitive function evaluation method according to an aspect of the present disclosure is executed by a computer. The cognitive function evaluation method includes: outputting a sentence to be uttered by an evaluatee; obtaining utterance data indicating a voice of the evaluatee uttering the sentence; calculating, from the utterance data obtained in the obtaining, a feature based on the utterance data; evaluating a cognitive function of the evaluatee by comparing the feature calculated in the calculating to reference data indicating a relationship between voice data indicating a voice of a person and a cognitive function of the person; and outputting a result of the evaluating.

The present disclosure may be implemented as a non-transitory computer-readable storage medium storing a program for causing the computer to execute the cognitive function evaluation method.

Advantageous Effect of Invention

A cognitive function evaluation device, for example, according to the present disclosure allows simple and accurate evaluation on the cognitive function of an evaluatee.

DESCRIPTION OF EXEMPLARY EMBODIMENT

Now, an embodiment will be described with reference to the drawings. Note that the embodiment described below is a mere comprehensive or specific example of the present disclosure. The numerical values, shapes, materials, constituent elements, the arrangement and connection of the constituent elements, steps, step orders etc. shown in the following embodiment are thus mere examples, and are not intended to limit the scope of the present disclosure. Among the constituent elements in the following embodiment, those not recited in any of the independent claims defining the broadest concept of the present disclosure are described as optional constituent elements.

The figures are schematic representations and not necessarily drawn strictly to scale. In the figures, substantially the same constituent elements are assigned with the same reference marks, and redundant descriptions will be omitted or simplified.

The following embodiment employs expressions for directions. For example, "horizontal" means not only "completely horizontal" but also "substantially horizontal", that is, including differences of about several percent, for example.

Embodiment

Configuration of Cognitive Function Evaluation Device

Figure 1:
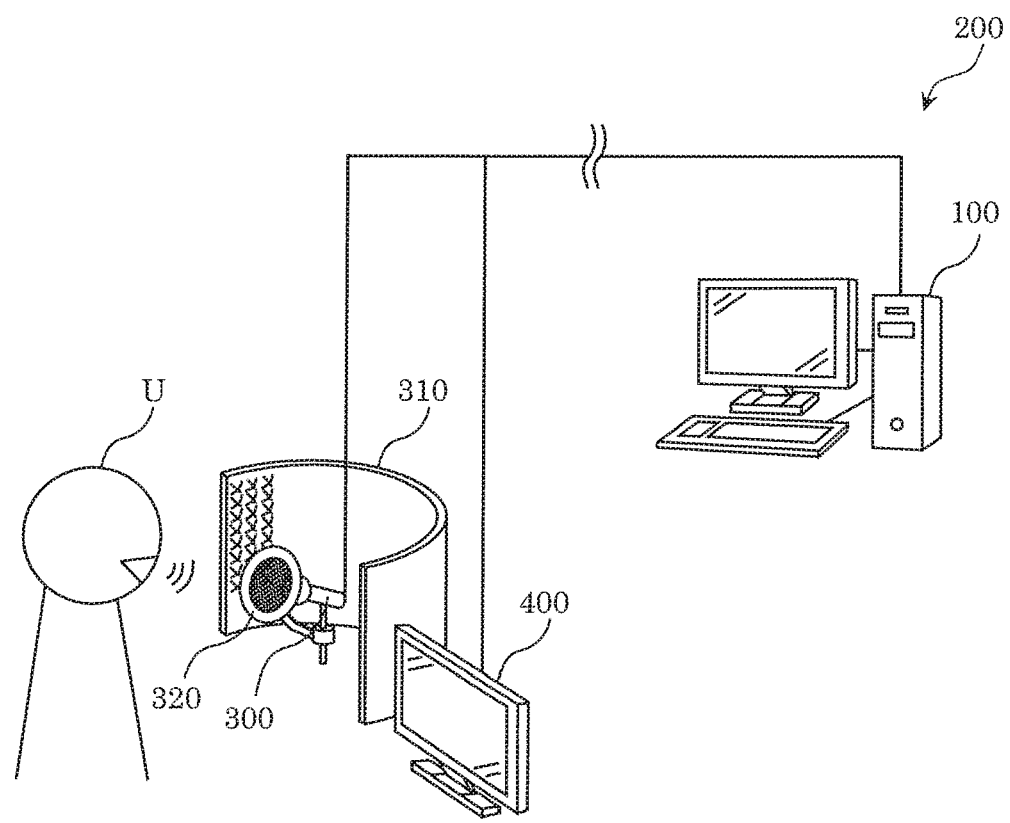
FIG. 1 shows a configuration of a cognitive function evaluation system according to an embodiment.

A configuration of a cognitive function evaluation system according to the embodiment will be described. FIG. 1 shows the configuration of the cognitive function evaluation system according to the embodiment.

Cognitive function evaluation system 200 is for evaluating the cognitive function of evaluatee U from the voice of evaluatee U. The cognitive function represents capabilities such as recognition, remembering, or judgment. As a specific example, cognitive function evaluation device 100 evaluates whether evaluatee U has dementia (i.e., whether the evaluatee is a dementia patient).

The symptoms of dementia include a decline in the cognitive function described above. Specific examples of dementia include Alzheimer's disease (AD). Since dementia patients are often not aware of any symptoms, the family of a suspected dementia patient or a third person encourages him/her to receive a medical examination at a hospital. Only then, the suspected patient sees a doctor. Alternatively, evaluatee U takes a batch test for dementia, such as the Montreal cognitive assessment (MoCA) test, to check whether evaluatee U has dementia.

The MoCA test takes, however, about 15 minutes each time. The MoCA test needs to be conducted a plurality of times at an interval to examine evaluatee U's change over time, thereby determining whether evaluatee U has dementia. That is, one set of the MoCA test requires a long time to examine whether evaluatee U has dementia.

It is known that there tends to be a difference in the voice between dementia patients and non-dementia people (i.e., healthy people), even when they utter the same word.

Cognitive function evaluation system 200 analyzes the voice of evaluatee U, thereby accurately evaluating the cognitive function level of evaluatee U.

As shown in FIG. 1, cognitive function evaluation system 200 includes cognitive function evaluation device 100, voice collection device 300 that detects the voice of evaluatee U, and display device 400.

Cognitive function evaluation device 100 is a computer that evaluates the cognitive function of evaluatee U from utterance data (i.e., voice data) obtained by voice collection device 300 and indicating the voice of evaluatee U. Specifically, cognitive function evaluation device 100 causes display device 400 to display sentence data indicating a certain sentence to be uttered by evaluatee U (i.e., image data including the sentence). The device obtains utterance data indicating the voice of evaluatee U via voice collection device 300.

Voice collection device 300 is a microphone that detects the voice of evaluatee U and outputs utterance data indicating the detected voice to cognitive function evaluation device 100. In order to accurately detect the voice of evaluatee U, at least one of isolation shield 310 or pop guard 320 may be arranged around voice collection device 300.

Display device 400 displays images based on image data output from cognitive function evaluation device 100. Specifically, display device 400 obtains and displays sentence data and the result of the evaluation on the cognitive function of evaluatee U. The sentence data is output from output unit 140 (see, e.g., FIG. 2), which will be described later, and indicates the sentence to be uttered by evaluatee U. Specifically, display device 400 is a monitor device such as a liquid crystal panel or an organic EL panel. Display device 400 may be an information terminal such as a television, a smartphone, or a tablet terminal.

Cognitive function evaluation device 100, voice collection device 300, and display device 400 may be connected in a wired or wireless fashion, as long as capable of sending and receiving utterance data or image data.

Cognitive function evaluation device 100 analyzes the voice of evaluatee U based on the utterance data detected by voice collection device 300, evaluates the cognitive function of evaluatee U from the result of the analyzation, and outputs an image indicating the result of the evaluation to display device 400. This configuration causes cognitive function evaluation device 100 to notify a dementia patient, who is not aware of any symptoms, of the cognitive function level and thus to encourage the dementia patient, for example, to see a doctor. In other words, cognitive function evaluation device 100 notifies a dementia patient, who is not aware of any symptoms, of the cognitive function level, thereby encouraging the dementia patient to see a doctor.

Note that cognitive function evaluation device 100 is a personal computer, for example, but may be a server device.

Figure 2:
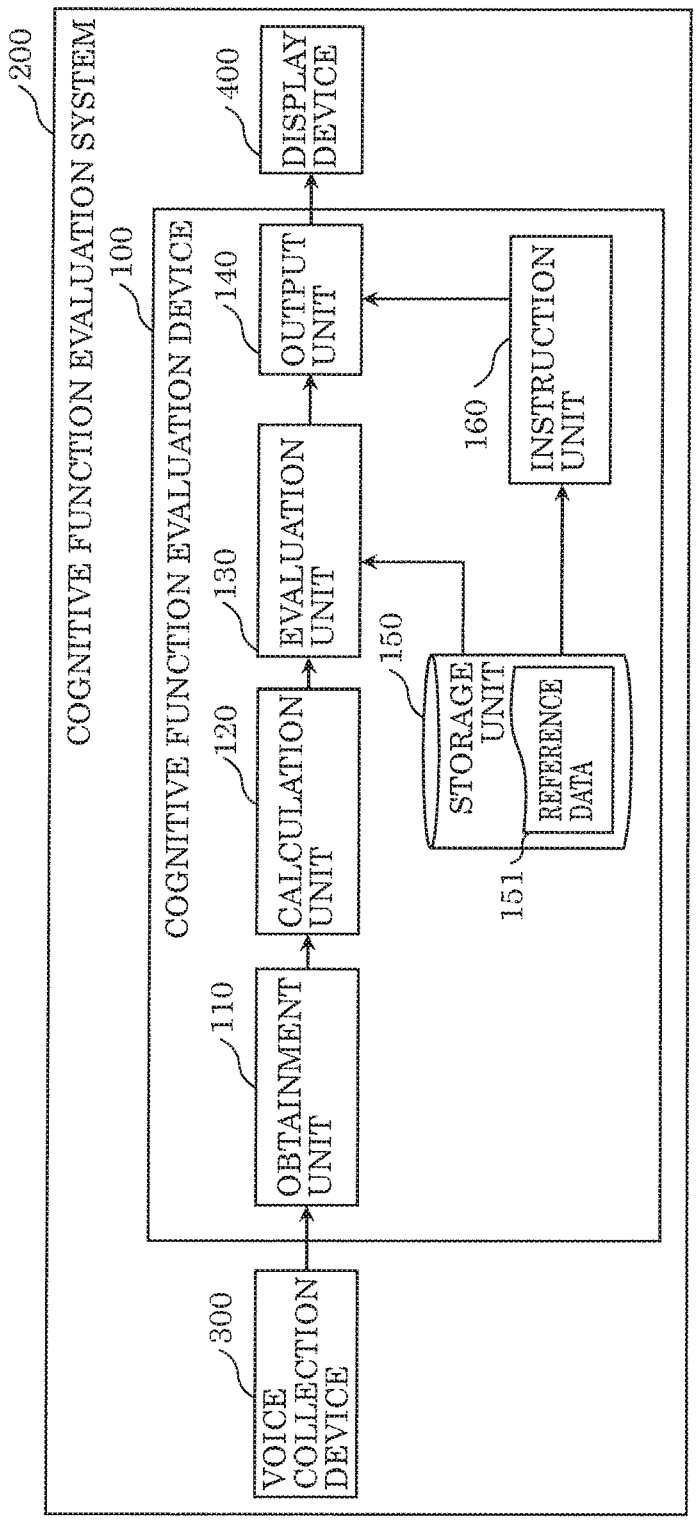
FIG. 2 is a block diagram showing characteristic functional configurations of a cognitive function evaluation device and the cognitive function evaluation system according to the embodiment.

FIG. 2 is a block diagram showing a characteristic functional configuration of cognitive function evaluation device 100 according to the embodiment. Cognitive function evaluation device 100 includes obtainment unit 110, calculation unit 120, evaluation unit 130, output unit 140, storage unit 150, and instruction unit 160.

Obtainment unit 110 obtains utterance data indicating the voice of evaluatee U uttering a sentence as instructed. Specifically, the obtainment unit obtains the utterance data detected by voice collection device 300. Obtainment unit 110 is a communication interface that performs wired or wireless communications, for example.

Calculation unit 120 is a processing unit that analyzes the utterance data on evaluatee U obtained by obtainment unit 110 to calculate a feature based on the utterance data. Specifically, calculation unit 120 may be configured as hardware using a processor, a microcomputer, or a dedicated circuit.

For example, the sentence indicated by the sentence data output from output unit 140 contains a character string with consecutive syllables, each of which consists of a vowel. Calculation unit 120 may calculate, as the feature, at least one of the amounts of changes in the first and second formant frequencies of the vowel, the times required for the changes in the first and second formant frequencies of the vowel, or the rates of changes that are the ratios of the amounts of changes to the required times.

The first formant frequency is a peak frequency of the amplitude that can be seen first, counting from the lowest frequency of the human voice. It is known that the first formant frequency tends to reflect the feature related to the movement of the tongue. As compared to healthy people, dementia patients often fail to move their tongue well. It is thus considered that there tends to be a difference in the first formant frequency between healthy people and dementia patients.

The second formant frequency is a peak frequency of the amplitude that can be seen second, counting from the lowest frequency of the human voice. It is known that the second formant frequency tends to reflect the influence related to the position of the tongue, out of the resonance caused by the vocal cord sound source in the vocal tract, the nasal cavity, and the oral cavity such as lips, and the tongue. As compared to healthy people, dementia patients often suffer from a decline in the motor function maintaining the position of the tongue or the chin. It is thus considered that there tends to be a difference in the second formant frequency and the amplitude between healthy people and dementia patients.

For example, the sentence indicated by the sentence data output from output unit 140 may contain a plurality of syllables, each of which includes a vowel. Calculation unit 120 may calculate, as the feature, a variation in at least one of the first formant frequency of the vowel, the second formant frequency of the vowel, or the ratio of the second formant frequency of the vowel to the first formant frequency of the vowel. The degree of variation calculated as the feature is, for example, a standard deviation.

For example, the sentence indicated by the sentence data output from output unit 140 may contain at least three syllables including different vowels. Calculation unit 120 may calculate, as the feature, at least one of the shape or the area of the polygon defined by plotting the value of the second formant frequency with respect to the first formant frequency calculated from each of the at least three vowels in the coordinate space defined by the second formant frequency of the vowel with respect to the first formant frequency of the vowel.

For example, the sentence indicated by the sentence data output from output unit 140 may contain at least two syllables including different vowels. Calculation unit 120 may calculate, as the feature, the positional relationship when plotting the value of the second formant frequency with respect to the first formant frequency calculated from the at least two vowels in the coordinate space defined by the second formant frequency of the vowel with respect to the first formant frequency of the vowel.

For example, the sentence indicated by the sentence data output from output unit 140 may contain a syllable including a consonant and a vowel subsequent to the consonant (i.e., a subsequent vowel). Calculation unit 120 may calculate, as the feature, the difference in the voice pressure between the consonant and the subsequent vowel. Note that, in this specification, the subsequent vowel is the phoneme that is a vowel such as "a", "i", "u", "e", or "o" subsequent to the phoneme that is a consonant such as "k", "s", "t", "n", or "h". For example, "ta" includes "t" as a consonant and "a" as a subsequent vowel following the consonant. For example, in the case of "ta", the difference in the voice pressure between the consonant and the subsequent vowel corresponds to the difference between the voice pressure of "t" and the voice pressure of "a". Examples of the "consonant and the subsequent vowel following the consonant" include what is called "open syllables" except for syllables, each of which consists of a vowel only. In particular, the consonant employed in calculating the feature may be a stop consonant (i.e., what is called a "plosive") such as "p", "t", or "k" that tends to cause a difference between healthy people and dementia patients.

For example, calculation unit 120 may calculate, as the feature, the time required by evaluatee U to utter the sentence.

For example, output unit 140 may further output an instruction that causes evaluatee U to utter a sentence a plurality of times. Calculation unit 120 may calculate, as the feature, the amount of change in the reading time calculated from reading times obtained for the plurality of times U evaluatee uttered the sentence.

Evaluation unit 130 compares a plurality of features that are ones calculated by calculation unit 120 or selected freely to reference data 151 stored in storage unit 150 to evaluate the cognitive function of evaluatee U. For example, storage unit 150 stores, as reference data 151, a threshold of a feature for distinguishing healthy people, mild dementia patients, and dementia patients from each other. Evaluation unit 130 compares the feature calculated by calculation unit 120 and the threshold stored as reference data 151 to evaluate that evaluatee U is a healthy person, a mild dementia patient, or a dementia patient. Evaluation unit 130 is a processor, a microcomputer, or a dedicated circuit, for example. Note that calculation unit 120 and evaluation unit 130 may be integrated in a single processor, a microcomputer, or a dedicated circuit with corresponding functions, or may be achieved by a combination of two or more of processors, microcomputers, and dedicated circuits.

Output unit 140 outputs sentence data (i.e., image data) indicating a certain sentence to be uttered by evaluatee U and the result of the evaluation on the cognitive function of evaluatee U by evaluation unit 130 to display device 400. Output unit 140 is a communication interface that performs wired or wireless communications, for example. For example, the sentence indicated by the sentence data output from output unit 140 may contain a character string of at least one of consecutive syllables, each of which consists of a consonant and a vowel subsequent to the consonant (i.e., a subsequent vowel), or consecutive syllables, each of which consists of a vowel only. That is, the sentence indicated by the sentence data output from output unit 140 may contain a character string of consecutive open syllables.

For example, the sentence indicated by the sentence data output from output unit 140 may contain five or more characters, each of which consists of a stop consonant and a subsequent vowel. Specifically, the sentence indicated by the sentence data output from output unit 140 may contain at least one of character strings "Kitakaze to taiyo ga deteimasu", "Tankenka wa bouken ga daisuki desu", or "Kita kara kita kata tatakiki".

Storage unit 150 is a storage device that stores reference data 151 indicating the relationship between a feature based on voice data indicating the voices of people and the cognitive functions of the people. Reference data 151 is referenced by evaluation unit 130 in evaluating the cognitive function of evaluatee U and stored in advance in storage unit 150. Storage unit 150 is read-only memory (ROM), a random-access memory (RAM), for example.

Storage unit 150 also stores programs executed by calculation unit 120 and evaluation unit 130, image data including the sentence to be uttered by evaluatee U, and image data to be used in outputting the result of the evaluation on the cognitive function of evaluatee U and indicating the result of the evaluation.

Instruction unit 160 is a control device that causes output unit 140 to output the sentence data indicating the sentence to be uttered by evaluatee U. Instruction unit 160 is communicatively coupled to cognitive function evaluation device 100, for example. The instruction unit obtains an instruction indicating start of evaluation on the cognitive function of evaluatee U from a user interface (not shown), such as a touch panel or buttons, operated by a user (e.g., evaluatee U or an assistant of evaluatee U) of cognitive function evaluation device 100. Upon receipt of the instruction, the instruction unit causes output unit 140 to output image data (e.g., image 410 shown in (a) of FIG. 4) stored in storage unit 150 prepared in advance to instruct evaluatee U to utter a certain sentence. Specifically, instruction unit 160 is a processor, a microcomputer, or a dedicated circuit. Note that calculation unit 120, evaluation unit 130, and instruction unit 160 may be integrated in a single processor, a microcomputer, or a dedicated circuit with corresponding functions, or may be achieved by a combination of two or more of processors, microcomputers, and dedicated circuits. Control programs executed by instruction unit 160 may be stored in storage unit 150.

Processing Procedure of Cognitive Function Evaluation Method

Now, a specific processing procedure of a cognitive function evaluation method executed by cognitive function evaluation device 100 will be described.

First, output unit 140 outputs sentence data stored in storage unit 150 and indicating the sentence to be uttered by evaluatee U to display device 400 (step S101). Specifically, in step S101, instruction unit 160 causes output unit 140 to output sentence data stored in storage unit 150 and indicating a certain sentence that instructs evaluatee U to utter a sentence. Display device 400 displays an image indicated by the sentence data obtained from output unit 140.

Next, obtainment unit 110 obtains utterance data on evaluatee U via voice collection device 300 (step S102). In step S102, for example, evaluatee U utters a sentence such as "Kita kara kita kata tatakiki" displayed on display device 400. Obtainment unit 110 obtains, as the utterance data, the voice of evaluatee U uttering the sentence "Kita kara kita kata tatakiki" via voice collection device 300.

After that, calculation unit 120 calculates the feature based on the utterance data obtained in step S102 (step S103). In step S103, for example, calculation unit 120 extracts "ta" uttered first in "Kita kara kita kata tatakiki" contained in the utterance data and calculates, as the feature, the difference in the voice pressure between the consonant and the subsequent vowel of the extracted "ta".

As described above, the feature calculated by calculation unit 120 is not limited thereto. Specific examples of the feature calculated by calculation unit 120 which will be described later.

Next, evaluation unit 130 evaluates the cognitive function of evaluatee U from the feature calculated by calculation unit 120 in step S103 (step S104). In step S104, evaluation unit 130 evaluates the cognitive function of evaluatee U from, for example, the feature calculated by calculation unit 120 in step S103 and reference data 151 stored in storage unit 150.

After that, output unit 140 outputs the result of the evaluation on the cognitive function of evaluatee U by evaluation unit 130 (step S105). In step S105, output unit 140 obtains, for example, an image corresponding to the result of the evaluation by evaluation unit 130 in step S104 from storage unit 150 and sends the obtained image to display device 400.

Display device 400 obtains the image output from output unit 140 and displays the image. Accordingly, evaluatee U easily knows the result of the evaluation on the cognitive function.

Figure 3:
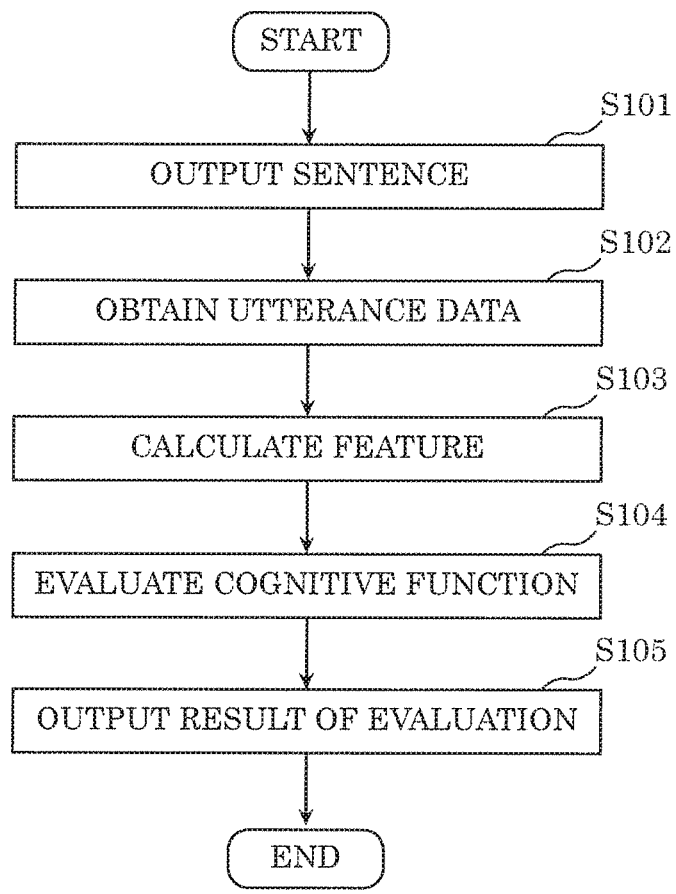
FIG. 3 is a flowchart showing a processing procedure of the cognitive function evaluation device according to the embodiment evaluating the cognitive function of an evaluatee.
Figure 4:
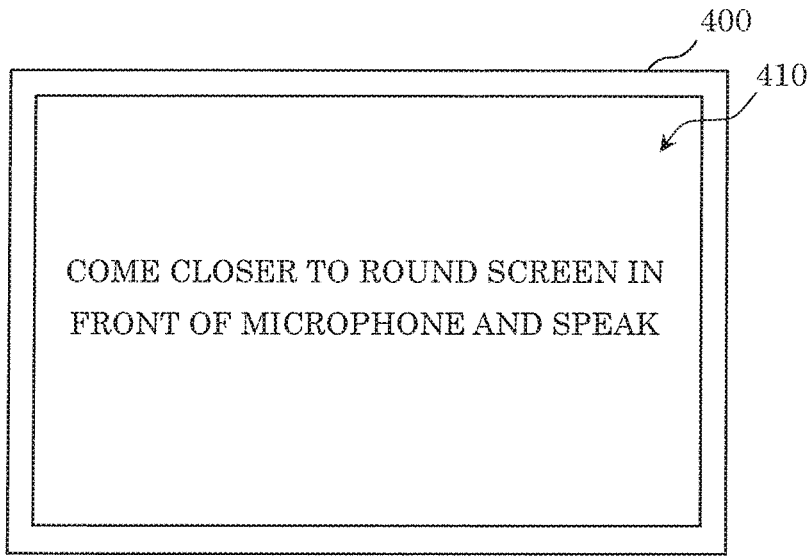
FIG. 4 shows an example method of obtaining the utterance data on the evaluatee using an obtainment unit.
Figure 4:
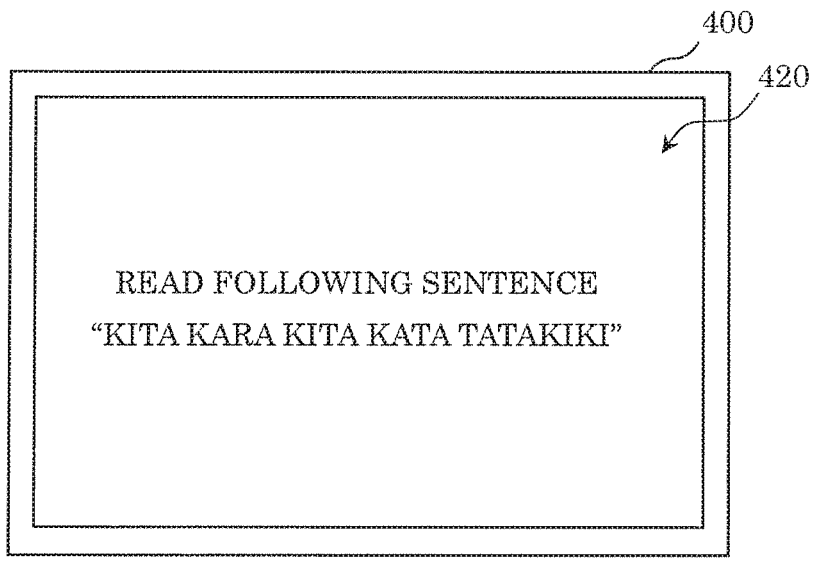
Figure 4:

FIG. 4 shows an example method of obtaining the voice data on evaluatee U using obtainment unit 110 in step S101 shown in FIG. 3. Specifically, (a) of FIG. 4 shows an example of image 410 displayed on display device 400 before cognitive function evaluation device 100 causes evaluatee U to utter a sentence. In FIG. 4, (b) shows an example of image 420 displayed on display device 400 when cognitive function evaluation device 100 obtains the utterance data on evaluatee U. In FIG. 4, (c) shows evaluatee U uttering the sentence displayed on display device 400.

As shown in (a) of FIG. 4, cognitive function evaluation device 100 causes display device 400 to display image 410 containing a sentence "Come closer to the round screen in front of the microphone and speak" for evaluatee U before obtaining the utterance data from evaluatee U. The content of the sentence shown in (a) of FIG. 4 may be, for example, explained directly to evaluatee U by a doctor or any other practitioner or may be listened as recorded voice to by evaluatee U.

Next, as shown in (b) of FIG. 4, display device 400 displays image 420 containing a sentence to be uttered by evaluatee U. As shown in (b) of FIG. 4, image 420 is displayed which contains the sentence of "Kita kara kita kata tatakiki", for example.

After that, as shown in (c) of FIG. 4, evaluatee U utters the sentence contained in image 420. In the example shown in (c) of FIG. 4, calculation unit 120 extracts, for example, "ta" uttered first in the sentence "Kita kara kita kata tatakiki". Calculation unit 120 calculates the voice pressures of "t" as the consonant and "a" as the subsequent vowel in the extracted "ta", and calculates, as the feature, the difference in the voice pressure between "t" and "a" from the calculated voice pressures.

In this manner, the sentence to be uttered by evaluatee U is displayed as image 420 not to cause a noise when detecting the voice of evaluatee U, as compared to the case where a doctor or any other practitioner tells the contents of the sentence to evaluatee U.

Details of the Feature

Now, details of the feature used when cognitive function evaluation device 100 evaluates the cognitive function level of evaluatee U will be described.

Figure 5:
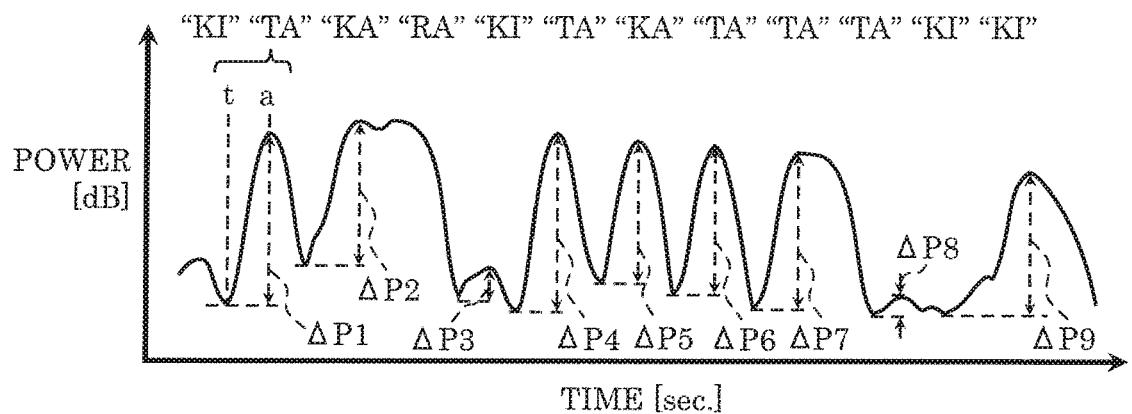
FIG. 5 shows example utterance data indicating the voice of the evaluatee.

FIG. 5 shows example utterance data indicating the voice of evaluatee U. Specifically, FIG. 5 is a graph showing utterance data when evaluatee U utters the sentence "Kita kara kita kata tatakiki". In the graph shown in FIG. 5, the horizontal axis represents the time, whereas the vertical axis represents power (i.e., the voice pressure). Decibel (dB) is used as the unit of the power represented by the vertical axis of the graph of FIG. 5.

In the graph shown in FIG. 5, variations in the voice pressure are found which correspond to "ki", "ta", "ka", "ra", "ki", "ta", "ka", "ta", "ta", "ta", "ki", and "ki". In step S102 shown in FIG. 3, obtainment unit 110 obtains, as the utterance data from evaluatee U, the data shown in FIG. 5. For example, in step S103 shown in FIG. 3, calculation unit 120 calculates the voice pressures of "t" and "a" of "ta", which appears first, from the utterance data shown in FIG. 5 by a known method. Calculation unit 120 calculates, as the feature, difference $\Delta P1$ in the voice pressure between "t" and "a" from the calculated voice pressures of "t" and "a". In this case, reference data 151 contains a threshold that is difference $\Delta P1$ in the voice pressure. For example, evaluation unit 130 determines that evaluatee U has dementia, if the difference is larger than or equal to the threshold; and evaluates the evaluatee as a healthy person, if the difference is smaller than the threshold.

Note that the feature may be a variation in the standard deviation among a plurality of differences in the voice pressure. In this case, calculation unit 120 calculates, for example, differences ΔP1 to ΔP9 in the voice pressure shown in FIG. 5 and calculates, as the feature, the standard deviation among differences ΔP1 to ΔP9 in the voice pressure. As compared to healthy people, dementia patients have a large standard deviation among the differences in the voice pressure. If the standard deviation among the differences in the voice pressure is employed as the feature, reference data 151 contains a threshold that is the value of the standard deviation. For example, evaluation unit 130 determines that evaluatee U has dementia, if the value is greater than or equal to the threshold; and evaluates the evaluatee as a healthy person, for example, if the value is smaller than the threshold. The number of the differences in the voice pressure used in calculating the standard deviation is not particularly limited and may be two, three, or more.

Figure 6:
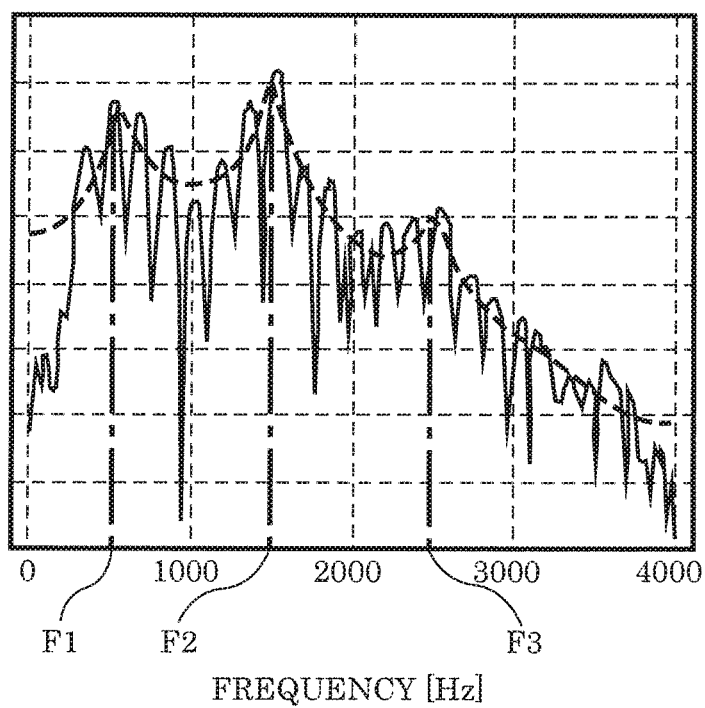
FIG. 6 illustrates a formant frequency calculated from the utterance data by a calculation unit.

FIG. 6 illustrates formant frequencies calculated from the utterance data by calculation unit 120. In the graph shown in FIG. 6, the horizontal axis represents the frequency [Hz], whereas the vertical axis represents the amplitude.

As indicated by the broken lines in FIG. 6, a plurality of peaks are found in the data obtained by converting the horizontal axis of the utterance data into the frequency. Out of the peaks, first formant frequency F1 has the lowest peak. Second formant frequency F2 has the second lowest peak next to first formant frequency F1. Third formant frequency F3 has the third lowest peak next to second formant frequency F2. In this manner, calculation unit 120 extracts a vowel from the utterance data, which has been obtained by obtainment unit 110, by a known method. The calculation unit then convers the utterance data on the extracted vowel into the amplitude of the frequency to calculate the spectrum of the vowel, thereby calculating the formant.

According to the graph shown in FIG. 6, the calculation is made by converting the utterance data obtained from evaluatee U into data on the amplitude of the frequency and then obtaining the envelope of the data. The envelope may be calculated by cepstral analysis or linear predictive coding (LPC), for example.

Figure 7:
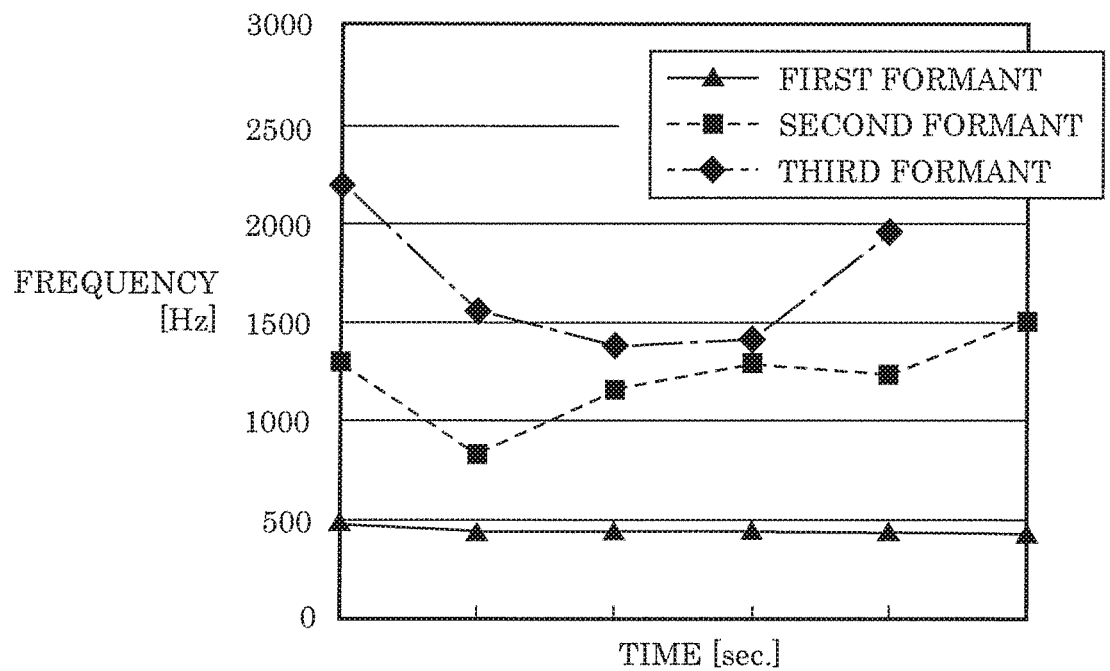
FIG. 7 shows example time changes in formant frequencies calculated from the utterance data by the calculation unit.

FIG. 7 shows example time changes in formant frequencies calculated from the voice data by calculation unit 120. Specifically, FIG. 7 is a graph for illustrating example time changes in first formant frequency F1, second formant frequency F2, and third formant frequency F3.

For example, cognitive function evaluation device 100 causes evaluatee U to utter syllables including consecutive vowels such as "aiueo". Specifically, output unit 140 outputs, to display device 400, sentence data indicating a sentence containing a character string of the syllables including the consecutive vowels such as "aiueo" to cause display device 400 to display the sentence. This causes evaluatee U to utter the syllables including the consecutive vowels such as "aiueo". Calculation unit 120 calculates first formant frequency F1 and second formant frequency F2 of each vowel from the utterance data indicating the voice of evaluatee U. In addition, calculation unit 120 calculates, as the feature, at least one of the amounts of changes in first formant frequency F1 and second formant frequency F2 of each consecutive vowel of the character string, the times required for the changes in first formant frequency F1 and second formant frequency F2 of each consecutive vowel of the character string, or the rates of the changes that are the ratios of the amounts of changes to the required times.

As compared to healthy people, dementia patients have large amounts, long times, and high rates of changes in first formant frequency F1 and second formant frequency F2. If one of the amounts of changes, the required times, or the rates of changes is employed as the feature, reference data 151 contains a threshold that is the value of one of the amounts of changes, the required times, or the rates of changes. For example, evaluation unit 130 determines that evaluatee U has dementia, if the value is greater than or equal to the threshold; and evaluates the evaluatee as a healthy person, for example, if the value is smaller than the threshold.

The vowels contained in the sentence uttered by evaluatee U may not be consecutive. Specifically, output unit 140 may output, to display device 400, sentence data indicating a sentence containing a character string of inconsecutive vowels, such as "i" and "u" of "taiyou" to cause display device 400 to display the sentence. In this case, calculation unit 120 may calculate, as the feature, a variation in at least one of first formant frequency F1 of each vowel, second formant frequency F2 of each vowel, or the ratio of second formant frequency vowel F2 of each vowel to first formant frequency F1 of the vowel. The degree of variation calculated as the feature is, for example, a standard deviation. As compared to healthy people, dementia patients have a larger variation. If the variation (specifically, the standard deviation) is employed as the feature, reference data 151 contains a threshold that is the value of the standard deviation. For example, evaluation unit 130 determines that evaluatee U has dementia, if the value is greater than or equal to the threshold, evaluates the evaluatee as a healthy person, for example, if the value is smaller than the threshold.

A sentence such as "Kita kara kita kata tatakiki" contains no syllables consisting of a vowel only but open syllables, each of which consists of a consonant and a subsequent vowel. In this case, calculation unit 120 may extract, for example, the phoneme of a subsequent vowel and calculate the formant frequency of the subsequent vowel to calculate the amounts of a change, the required time, or the rate of change in the formant frequency. Each character string of the consecutive vowels may be a character string of a subsequent vowel and a vowel following the subsequent vowel.

Note that cognitive function evaluation device 100 may include a time measurement unit such as a real time clock (RTC) to measure the time.

Figure 8:
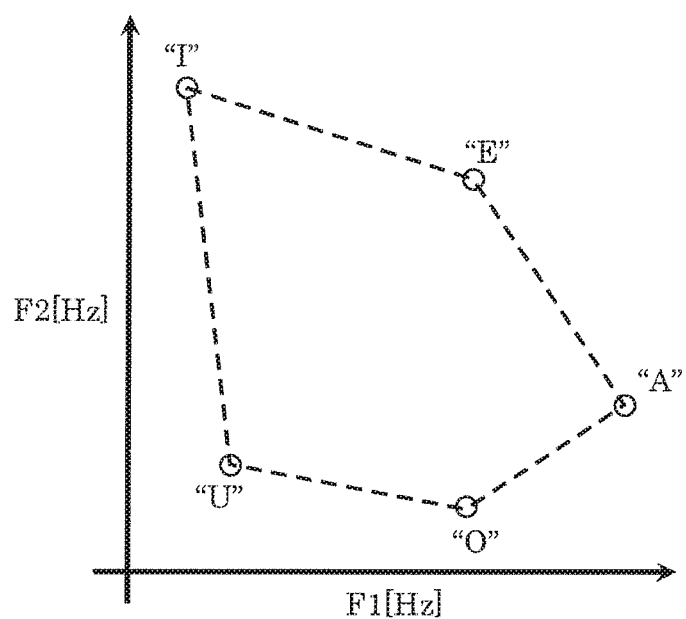
FIG. 8 illustrates an example feature of the utterance data evaluated by an evaluation unit.

FIG. 8 illustrates an example feature of utterance data to be evaluated by evaluation unit 130. In the graph shown in FIG. 8, the horizontal axis represents first formant frequency F1, whereas the vertical axis represents second formant frequency F2.

As shown in FIG. 8, calculation unit 120 calculates first formant frequency F1 and second formant frequency F2 of a single vowel and plots the result at a single point in the graph shown in FIG. 8. For example, evaluatee U utters "a", "i", "u", "e", "o". Specifically, output unit 140 outputs, to display device 400, the sentence data indicating the sentence containing "a", "i", "u", "e", and "o" to cause display device 400 to display the sentence. This causes evaluatee U to utter "a", "i", "u", "e", "o". Calculation unit 120 calculates first formant frequency F1 and second formant frequency F2 of each of "a", "i", "u", "e", and "o" contained in the utterance data. Accordingly, calculation unit 120 plots the point corresponding to each of "a", "i", "u", "e", and "o" in the coordinate space shown in FIG. 8. In this manner, calculation unit 120 calculates, as the feature, at least one of the shape or the area of the polygon defined by plotting the ratio of second formant frequency F2 to first formant frequency F1 calculated from each of the at least three vowels in the coordinate space. The coordinate space (specifically, the coordinate space shown in FIG. 8) is defined by second formant frequency F2 of the vowel with respect to first formant frequency F1 of the vowel.

As compared to healthy people, dementia patients have the polygon defined in this manner with a small area. If the area of the polygon is employed as the feature, reference data 151 contains a threshold that is the value of the area of the polygon. For example, evaluation unit 130 determines that evaluatee U is a healthy person, if the value is greater than or equal to the threshold; and evaluates the evaluatee as having dementia, for example, if the value is smaller than the threshold.

As compared to healthy people, dementia patients have the polygon defined in this manner in a shape with the points close to each other. Assume that the polygon is a pentagon and the shape of the polygon is approximated to a regular pentagon. As compared to healthy people, dementia patients have a polygon in a shape largely deviated from the regular pentagon. If the shape of the polygon is employed as the feature, reference data 151 contains a threshold that is the value of the distance between the points constituting the polygon, or the amount of deviation of each point when the pentagon is approximated to a regular pentagon. For example, evaluation unit 130 determines that evaluatee U is a healthy person, if the value is greater than or equal to the threshold; and evaluates the evaluatee as having dementia, for example, if the value is smaller than the threshold.

The vowels employed for plotting may be subsequent vowels subsequent to consonants. In a language other than Japanese, any other element such as "A", a phonetic symbol, may be used in addition to or in place of the vowels "a", "i", "u", "e", and "o" in the Japanese language.

The number of plotted points may be three or more, as long as at least one of the shape or the area of the polygon defined by the points can be calculated.

Figures 9, 10:
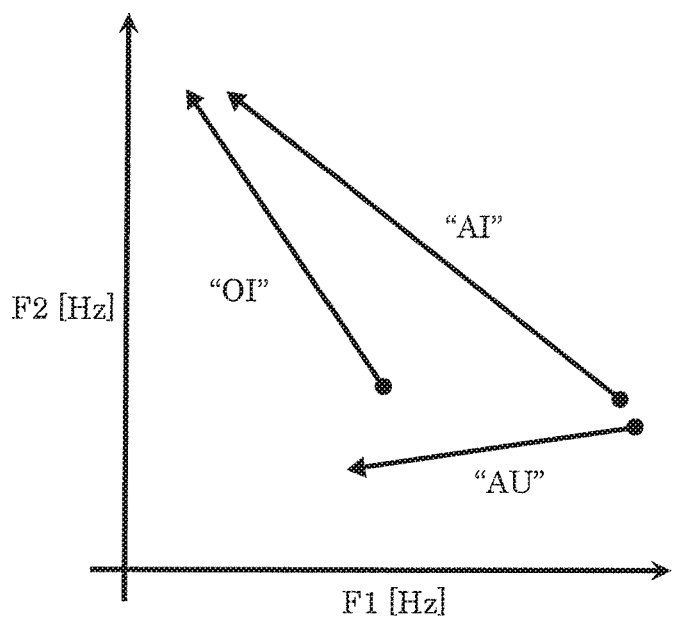
FIG. 9 illustrates another example feature of the utterance data evaluated by the evaluation unit.
FIG. 10 shows scores acquired by people in the MoCA test.

FIG. 9 illustrates another example feature of utterance data to be evaluated by evaluation unit 130.

As shown in FIG. 9, calculation unit 120 calculates first formant frequency F1 and second formant frequency F2 of a single vowel and plots the result at a single point in the graph shown in FIG. 9. For example, cognitive function evaluation device 100 causes evaluatee U to utter syllables including consecutive vowels such as "ai", "au", and "oi". Specifically, output unit 140 outputs, to display device 400, sentence data indicating the sentence containing a character string of the syllables including the consecutive vowels such as "ai", "au", and "oi" to cause display device 400 to display the sentence. This causes evaluatee U to utter, "ai", "au", and "oi", for example. Calculation unit 120 calculates first formant frequency F1 and second formant frequency F2 of each of "a" and "i" of "ai", for example, contained in the utterance data. Accordingly, calculation unit 120 plots the points corresponding to "a" and "i". In this manner, the sentence indicated by the sentence data output from output unit 140 may contain at least two consecutive vowels. Calculation unit 120 may calculate, as the feature, the positional relationship when plotting the ratio of second formant frequency F2 to first formant frequency F1 of the vowel calculated from each of the at least two respective vowels in the coordinate space (specifically, the coordinate space shown in FIG. 9) defined by second formant frequency F2 of the vowel with respect to first formant frequency F1 of the vowel.

As compared to healthy people, dementia patients have the points plotted in this manner at a small distance. If the positional relationship among the points is employed as the feature, reference data 151 contains a threshold that is the distance between the points. For example, evaluation unit 130 determines that evaluatee U is a healthy person, if the value is greater than or equal to the threshold; and evaluates the evaluatee as having dementia, for example, if the value is smaller than the threshold.

Whether a person has dementia is determined by the MoCA test, which is a batch test for examination of dementia, taken by the person.

FIG. 10 shows scores acquired by people in a MoCA test.

The present inventors gathered evaluatees including healthy people with normal controls (NC), mild dementia patients with mild cognitive impairment (MCI), and dementia patients with AD to conduct the MoCA test. The number of evaluatees (i.e., the number of subjects) with NC was 90, the number of evaluatees with MCI was 94, and the number of evaluatees with AD was 93.

It is found from FIG. 10 that the average scores in the MoCA test (i.e., the average MoCA scores) and the score ranges in the MoCA test (i.e., the MoCA score ranges) are different among the NC, MCI, and AD groups. Specifically, the average score of the NC group in the MoCA was 27.4, the average score of the MCI group in the MoCA was 22.1, and the average score of the AD group in the MoCA was 16.2.

The features, which are described above and based on the voice data (i.e., the utterance data) indicating the voices of the people, are calculated from the people who have taken the MoCA test. From the calculation, reference data 151 is prepared, which indicates the relationship between the features of the people and is based on the voice data and the cognitive functions of the people. For example, if evaluation unit 130 determines that evaluatee U has NC, MCI, or AD, reference data 151 corresponds to two thresholds (e.g., a first threshold and a second threshold) with different values as the threshold of the feature described above. For example, evaluation unit 130 evaluates evaluatee U as having NC, if the feature calculated from the utterance data obtained from evaluatee U is smaller than the first threshold. The evaluation unit evaluates evaluatee U as having MCI, if the feature is greater than or equal to the first threshold and smaller than the second threshold. The evaluation unit evaluates evaluatee U as having AD, if the feature is greater than or equal to the second threshold. Cognitive function evaluation device 100 uses reference data 151 to simply evaluate the cognitive function of evaluatee U from the feature based on utterance data on evaluatee U and reference data 151. Note that one, two, or more threshold(s) of the feature may be used as reference data 151.

Figure 11:
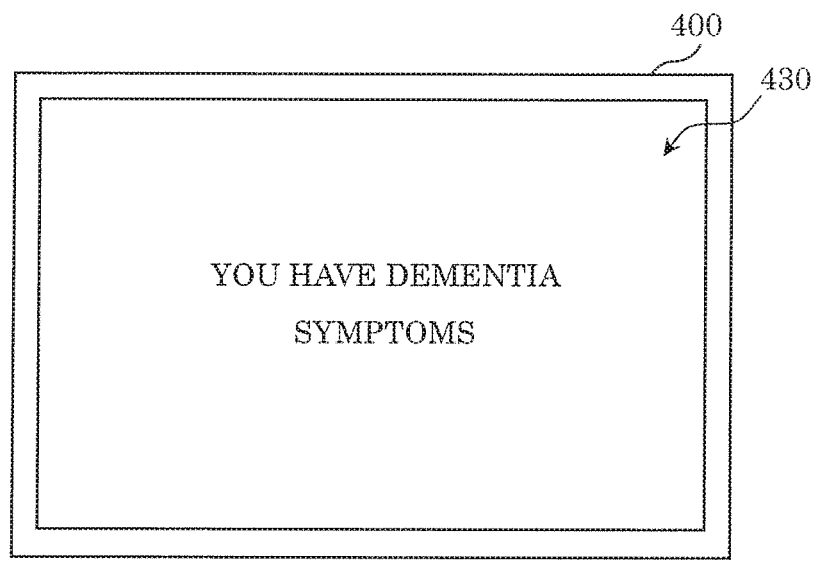
FIG. 11 shows an example image displayed on a display device and indicating a decline in the cognitive function.

FIG. 11 shows an example image displayed on display device 400 and indicating a decline in the cognitive function.

Display device 400 displays, as the result of the evaluation by evaluation unit 130, image 430 as shown in FIG. 11. Image 430 is an example image displayed if evaluation unit 130 evaluates the cognitive function of evaluatee U as having AD, for example. In this manner, display device 400 then displays, as an image, the result of the evaluation by evaluation unit 130. With this configuration, for example, if evaluatee U evaluates the cognitive function using cognitive function evaluation device 100 at home or any other place, cognitive function evaluation device 100 may encourage evaluatee U to see a doctor or any other practitioner.

Like "Kita kara kita kata tatakiki" shown in (c) of FIG. 4, the sentence may be uttered by evaluatee U not only once but also a plurality of times.

Figure 12:
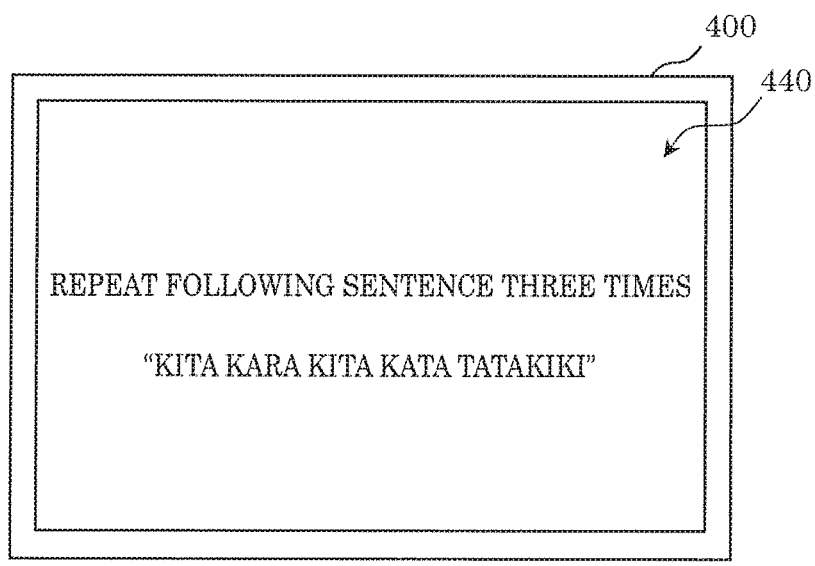
FIG. 12 shows another example image displayed on the display device in obtaining utterance data on the evaluatee.

FIG. 12 shows another example image displayed on display device 400 in obtaining the utterance data on evaluatee U.

Like image 440 shown in FIG. 12, the sentence data containing a sentence to be uttered by evaluatee U as instructed by output unit 140 may contain an explanation that causes the evaluatee to utter the sentence a plurality of times. For example, calculation unit 120 calculates, as the feature, the time required for evaluatee U to utter the sentence. As compared to healthy people, dementia patients need a long time to read a sentence. In this case, reference data 151 contains a threshold that is the reading time. For example, evaluation unit 130 determines that evaluatee U has dementia, if the value is greater than or equal to the threshold, and evaluates the evaluatee as a healthy person, for example, if the value is smaller than the threshold.

Evaluatee U here may utter a single sentence a plurality of times. Specifically, output unit 140 may further output an instruction that causes evaluatee U to utter the sentence the plurality of times. Calculation unit 120 may calculate, as the feature, the amount of change in the reading time calculated from reading times obtained for the plurality of times evaluatee U uttered the sentence.

For example, if the time required for evaluatee U to utter the sentence for the first time is ten seconds and the time required for evaluatee U to utter the sentence for the second time is eight seconds, the amount of change is two seconds. Alternatively, assume that evaluatee U utters a sentence three or more times. In this case, for example, calculation unit 120 may calculate, as the feature, the standard deviation of the time required for evaluatee U to utter the sentence each time, or the average of the amount of changes calculated the plurality of times.

As compared to healthy people, dementia patients have a large amount of change in the reading time for the sentence. In this case, reference data 151 contains the amount of change in the reading time. For example, evaluation unit 130 determines that evaluatee U has dementia, if the value is greater than or equal to the threshold, and evaluates the evaluatee as a healthy person, for example, if the value is smaller than the threshold.

While FIG. 12 illustrates an instruction that causes evaluatee U to utter the sentence three times, the sentence may be uttered two, four, or more times.

The sentence data containing the sentence to be uttered by evaluatee U as instructed by output unit 140 may contain an explanation that causes the evaluatee to utter a sentence a plurality of times or to utter a plurality of sentences.

Advantages

As described above, cognitive function evaluation device 100 according to the embodiment includes obtainment unit 110, calculation unit 120, evaluation unit 130, and output unit 140. Obtainment unit 110 obtains utterance data indicating the voice of evaluatee U uttering a sentence as instructed. Calculation unit 120 calculates, from the utterance data obtained by obtainment unit 110, a feature based on the utterance data. Evaluation unit 130 compares the feature calculated by calculation unit 120 to reference data 151 indicating a relationship between voice data indicating voices of people and cognitive functions of the people to evaluate the cognitive function of the evaluatee. Output unit 140 outputs the sentence to be uttered by evaluatee U and output a result of the evaluation by evaluation unit 130.

With this configuration, cognitive function evaluation device 100 obtains, from evaluatee U, the voice data from which the cognitive function is accurately evaluated by evaluation unit 130. Accordingly, cognitive function evaluation device 100 simply and accurately evaluates the cognitive function of evaluatee U.

For example, the sentence to be uttered by evaluatee U may contain a character string of at least one of consecutive syllables, each of which consists of a consonant and a vowel subsequent to the consonant, or consecutive syllables, each of which consists of a vowel only.

That is, the voice data evaluated by evaluation unit 130 may contain at least one of consecutive syllables, each of which consists of a consonant and a vowel subsequent to the consonant, or consecutive syllables, each of which consists of a vowel only. For example, it is found from FIG. 5 that the vowel "a" has a higher voice pressure than the consonant "t". In this manner, for example, at voice collection, voice collection device 300 easily collects vowels as compared to consonants. The evaluatee repeatedly utters at least one of a combination of a consonant and a vowel subsequent to the consonant, or a combination of vowels only. This allows analysis of the plurality of vowels, which leads to more accurate evaluation on the cognitive function of evaluatee U.

For example, the sentence to be uttered by evaluatee U may contain at least one of character strings of "Kitakaze to taiyo ga deteimasu", "Tankenka wa bouken ga daisuki desu", or "Kita kara kita kata tatakiki". Like these, the sentence indicated by the sentence data output from output unit 140 may contain five or more character strings, each of which includes a stop consonant and a vowel subsequent to the stop consonant. There tends to be a difference in the stop consonant between the voice data on the patients with AD and the people with NC. The sentence to be uttered by evaluatee U may thus be, for example, "Kitakaze to taiyo ga deteimasu", "Tankenka wa bouken ga daisuki desu", and "Kita kara kita kata tatakiki". This allows more accurate evaluation of the cognitive function of evaluatee U.

For example, the sentence to be uttered by evaluatee U may contain a character string of consecutive syllables, each of which includes a vowel. Calculation unit 120 may calculate, as the feature, at least one of the amounts of changes in first formant frequency F1 and second formant frequency F2 of the vowel, times required for the changes in first formant frequency F1 and second formant frequency F2 of the vowel, or the rates of changes that are the ratios of the amount of changes to the required times.

First formant frequency F1 is a peak frequency of an amplitude that can be seen first, counting from the lowest frequency of the human voice. It is known that the first formant frequency tends to reflect the feature related to the movement of the tongue. As compared to the people with NC, the patients with AD often fail to move their tongue well. It is thus considered that there tends to be a difference in first formant frequency F1 between the people with NC and the patients with AD. For example, the patients with AD often suffer from a decline in the motor function maintaining the position of the tongue or the chin. It is thus considered that the patients with AD thus utter an unstable voice as compared to the people with NC. It is thus considered that, since there are fluctuations in the voices of the patients with AD as compared to the people with NC, the time change in each of first formant frequency F1 and second formant frequency F2 tends to be large. In this point of view, one of the amounts of changes in first formant frequency F1 and second formant frequency F2, the required times, and the rates of changes that are the ratios of the amounts of changes to the required times is used as the feature to evaluate the cognitive function. This allows more accurate evaluation on the cognitive function of evaluatee U.

For example, the sentence to be uttered by evaluatee U may contain a plurality of syllables, each of which includes a vowel. Calculation unit 120 may calculate, as the feature, at least one of variations in first formant frequency F1 of the vowel, second formant frequency F2 of the vowel, or the ratio of second formant frequency F2 of the vowel to first formant frequency F1 of the vowel.

As described above, as compared to the people with NC, the patients with AD tend to utter a fluctuating voice, and thus first formant frequency F1 and second formant frequency F2 tend to vary. It is considered that there is an individual difference in the formant frequency. It is also considered that, there is a correlation between first formant frequency F1 and second formant frequency F2, which also depends on the individual difference. In this point of view, the variation in the ratio of second formant frequency F2 of the vowel to first formant frequency F1 of the vowel is used as the feature. This allows more accurate evaluation of the cognitive function of evaluatee U.

For example, the sentence to be uttered by evaluatee U may contain at least three syllables, each of which includes a vowel different from the vowels of the other syllables. Calculation unit 120 may calculate, as the feature, at least one of the shape or the area of the polygon defined by plotting the ratio of second formant frequency F2 to first formant frequency F1 calculated from the vowel of each of the at least three syllables in the coordinate space defined by second formant frequency F2 of the vowel with respect to first formant frequency F1 of the vowel.

As described above, as compared to healthy people, dementia patients have the polygon defined in this manner with a small area. As compared to healthy people, dementia patients have the polygon defined in this manner in a shape with the points close to each other. Assume that the polygon is a pentagon and the shape of the polygon is approximated to a regular pentagon. As compared to healthy people, dementia patients have a polygon in a shape largely deviated from the regular pentagon. In this point of view, at least one of the shape or the area of the polygon is employed as the feature, which allows more accurate evaluation on the cognitive function of evaluatee U.

For example, the sentence to be uttered by evaluatee U may contain at least two consecutive syllables, each of which includes a vowel different from the vowel of the other syllable. Calculation unit 120 may calculate, as the feature, the positional relationship when plotting the ratio of second formant frequency F2 to first formant frequency F1 calculated from the vowel of each of the at least two consecutive syllables in the coordinate space defined by second formant frequency F2 of the vowel with respect to first formant frequency F1 of the vowel.

As described above, as compared to healthy people, dementia patients have the points plotted in this manner at a small distance. In this point of view, the positional relationship between the points is employed as the feature, which allows more accurate evaluation on the cognitive function of evaluatee U.

For example, the sentence to be uttered by evaluatee U may contain a syllable including a consonant and a vowel subsequent to the consonant. Calculation unit 120 may calculate, as the feature, the difference in the voice pressure between the consonant and the vowel.

For example, evaluation unit 130 determines that evaluatee U has dementia, if the value is greater than or equal to the threshold, and evaluates the evaluatee as a healthy person, for example, if the value is smaller than the threshold. For example, the feature may be a variation in the standard deviation among a plurality of differences in the voice pressure. In this case, calculation unit 120 calculates differences ΔP1 to ΔP9 in the voice pressure shown in FIG. 5, for example, and calculates, as the feature, the standard deviation among difference ΔP1 to ΔP9 in the voice pressure. As compared to healthy people, dementia patients have a large standard deviation among the differences in the voice pressure. In this point of view, the difference in the voice pressure is employed as the feature, which allows more accurate evaluation on the cognitive function of evaluatee U.

For example, calculation unit 120 may calculate, as the feature, a time required for evaluatee U to utter the sentence.

As described above, as compared to healthy people, dementia patients need a long time to read a sentence. In this point of view, the reading time for the sentence is employed as the feature, which allows more accurate evaluation on the cognitive function of evaluatee U.

For example, output unit 140 may further output an instruction for causing evaluatee U to utter the sentence a plurality of times. Calculation unit 120 may calculate, as the feature, the amount of change in the reading time calculated when the evaluatee utters the sentence.

As described above, as compared to healthy people, dementia patients have a large amount of change in the reading time for a sentence. In this point of view, the amount of change in the reading time for the sentence is employed as the feature. This allows more accurate evaluation on the cognitive function of evaluatee U.

For example, cognitive function evaluation device 100 may include storage unit 150 that stores reference data 151.

That is, cognitive function evaluation device 100 may communicate with an external server device or any other device that stores reference data 151 to evaluate the cognitive function of evaluatee U. Alternatively, the device may include storage unit 150 being a storage device that stores reference data 151. With this configuration, cognitive function evaluation device 100 evaluates the cognitive function of evaluatee U without being connected to a network for communications with an external server device. This improves the convenience of cognitive function evaluation device 100.

Cognitive function evaluation system 200 according to the embodiment includes cognitive function evaluation device 100, voice collection device 300, and display device 400. Voice collection device 300 detects the voice of evaluatee U. Display device 400 displays the sentence and the result of the evaluation output from output unit 140.

With this configuration, cognitive function evaluation system 200 displays the sentence to be uttered by evaluatee U using display device 400, detects the voice of evaluatee U using voice collection device 300, evaluates the cognitive function of evaluatee U using cognitive function evaluation device 100, and displays the result of the evaluation using display device 400. That is, cognitive function evaluation system 200 obtains, from evaluatee U, voice data from which the cognitive function is accurately evaluated by evaluation unit 130. Accordingly, cognitive function evaluation device 200 simply and accurately evaluates the cognitive function of evaluatee U.

A cognitive function evaluation method according to the embodiment is executed by a computer (specifically, cognitive function evaluation device 100). The cognitive function evaluation method includes: outputting a sentence to be uttered by evaluatee U; obtaining utterance data indicating the voice of evaluatee U; calculating, from the utterance data obtained in the obtaining, a feature based on the utterance data; evaluating the cognitive function of evaluatee U by comparing the feature calculated in the calculating to reference data indicating a relationship between voice data indicating the voices of people and the cognitive functions of the people; and outputting the result of the evaluating.

With this feature, the cognitive function evaluation method according to the present disclosure allows obtainment of voice data from which the cognitive function is accurately evaluated, from evaluatee U. Accordingly, the cognitive function evaluation method according to the present disclosure allows simple and accurate evaluation on the cognitive function of evaluatee U.

The present disclosure may be implemented as a non-transitory computer-readable storage medium storing a program that causes a computer to execute the steps included in the cognitive function evaluation method.

Variations

Now, cognitive function evaluation systems according to Variation 1 and Variation 2 of the embodiment will be described. Note that substantially the same constituent elements are assigned with the same reference marks, and redundant descriptions may be omitted or simplified.

Figure 13:
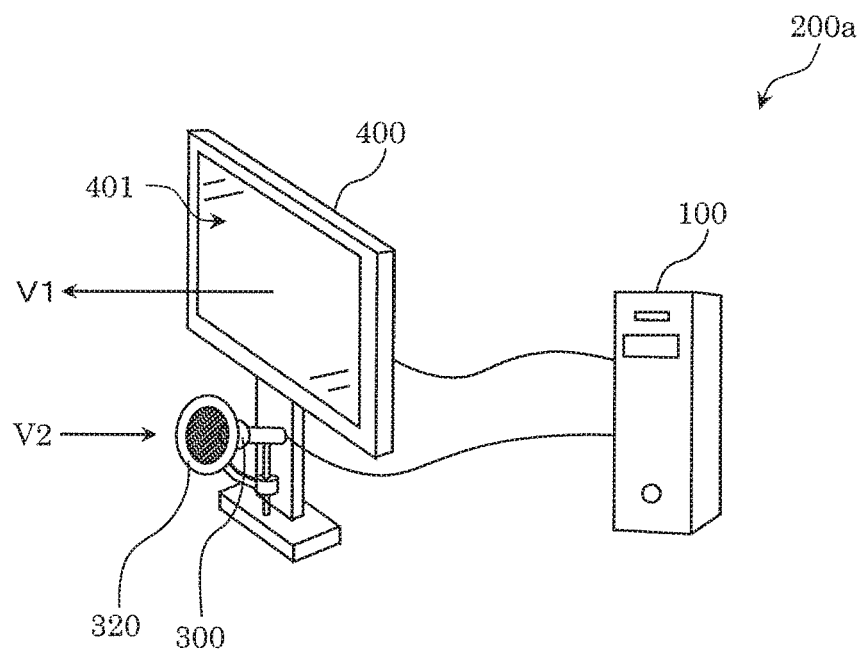
FIG. 13 shows a configuration of a cognitive function evaluation system according to Variation 1 of the embodiment.

FIG. 13 shows a configuration of the cognitive function evaluation system according to Variation 1 of the embodiment.

Like cognitive function evaluation system 200 according to the embodiment, cognitive function evaluation system 200a according to Variation 1 of the embodiment includes cognitive function evaluation device 100, voice collection device 300, and display device 400. Cognitive function evaluation system 200a may include pop guard 320 to cover voice collection device 300, for example.

Cognitive function evaluation system 200a employs directional voice collection device 300. Voice collection device 300 and display device 400 are here arranged such that the direction in which voice collection device 300 exhibits the maximum sensitivity (i.e., voice collection direction V2 shown in FIG. 13) agrees with normal direction V1 of display surface 401 on which display device 400 displays question information. Specifically, voice collection device 300 and display device 400 are arranged on a fixed object such as a desk such that normal direction V1 is parallel to voice collection direction V2. Note that voice collection device 300 and display device 400 may be fixed to a building material, for example. Cognitive function evaluation system 200a may include a fixture to establish a fixed positional relationship between voice collection device 300 and display device 400.

With this configuration, voice collection direction V2 tends to agree with the direction into which evaluatee U speaks even while viewing display device 400. The positional relationship as in cognitive function evaluation system 200a causes voice collection device 300 to accurately detect the voice of evaluatee U.

Now, a cognitive function evaluation system according to Variation 2 of the embodiment will be described.

Figure 14:
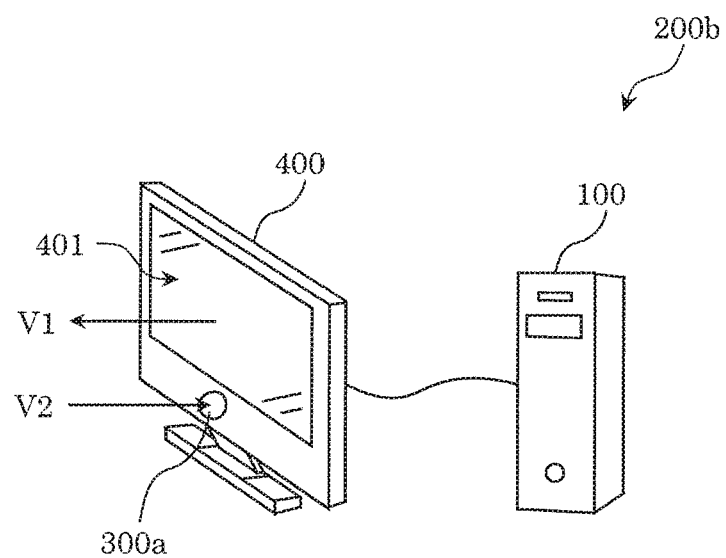
FIG. 14 shows a configuration of a cognitive function evaluation system according to Variation 2 of the embodiment.

FIG. 14 shows a configuration of the cognitive function evaluation system according to Variation 2 of the embodiment.

Like cognitive function evaluation system 200 according to the embodiment, cognitive function evaluation system 200b according to Variation 2 of the embodiment includes cognitive function evaluation device 100, voice collection device 300a, and display device 400.

Like voice collection device 300, voice collection device 300a is a microphone that detects the voice of evaluatee U and outputs voice data indicating the detected voice to cognitive function evaluation device 100. Like voice collection device 300 in cognitive function evaluation system 200a according to Variation 1 of the embodiment, voice collection device 300a is directional.

In cognitive function evaluation system 200b, voice collection device 300a and display device 400 are formed integrally. Specifically, voice collection device 300a and display device 400 are arranged in a housing. In the manufacturing process, voice collection device 300a and display device 400 may be integrally formed such that normal direction V1 agrees with voice collection direction V2. This may reduce the deviation between normal direction V1 and voice collection direction V2 when evaluatee U utilizes cognitive function evaluation system 200b.

Other Embodiments

The cognitive function evaluation devices or other elements have been described above in the embodiment and Variations 1 and 2 of the embodiment. The present disclosure is not limited to the embodiment and variations.

In the embodiment described above, Alzheimer's disease is named as a specific example of a decline in the cognitive function. The "cognitive function" represents, however, capabilities such as recognition, remembering, or judgment, and the "dementia" represents the symptoms of decreased cognitive function as described above. That is, the cognitive function evaluation device evaluates the cognitive function levels not only in Alzheimer's disease but also in vascular dementia or drunkenness, for example.

In the embodiment described above, in order to evaluate the cognitive function level of evaluatee U, the data indicating the relationship between the scores in the MoCA test and the features based on the formants is, as reference data 151, stored in advance in storage unit 150. However, the reference data may be any data as long as being compared to the features of the formants to allow evaluation on the cognitive function level. The reference data is not limited to the data indicating the relationship between the scores in the MoCA test and the features of the formants. For example, the reference data may be data indicating the relationship between scores in a mini-mental state examination (MMSE), for example, and the features of formants.

The embodiment described above includes the expressions such as "greater than or equal to the threshold" and "smaller than the threshold", which are not used in a strict sense. For example, the expression "greater than or equal to the threshold" may simply mean "greater than the threshold". The comparative expressions such as "greater than or equal to the threshold" and "smaller than the threshold" mean that distinction is made using the threshold as the boundary, and may also mean "greater than the threshold" and "smaller than or equal to the threshold", respectively.

The relationship between the utterance data and the degree of dementia in the reference data described above is based on data analysis of the evaluatees gathered by the present inventors at present. In the future, data analysis may be performed with more evaluatees or under modified conditions, which may change the evaluation standard. In the embodiment described above, the difference in the voice pressure is employed as the feature. For example, the evaluation unit determines that evaluatee U has dementia, if the value is greater than or equal to the threshold; and evaluates the evaluatee as a healthy person, for example, if the value is smaller than the threshold. The evaluation standard is not limited thereto. In this case, for example, the evaluation unit may determine that evaluatee U has dementia, if the value is smaller than the threshold; and evaluates the evaluatee as a healthy person, for example, if the value is greater than or equal to the threshold. It also applies to how to treat any other threshold as the feature.

In the embodiment described above, only the utterance data obtained from the evaluatee is calculated as the feature to evaluates the cognitive function of the evaluatee. The evaluation may be however performed by combining data sets that allow evaluation on other known cognitive functions. For example, it is known that there is a correlation between a cognitive function and walking data such as a step length, a step width, or a walking speed. A combination of the utterance data on the evaluatee evaluated in the embodiment described above and the walking data on the evaluatee may be used for the evaluation on the cognitive function, which leads to more accurate evaluation on the cognitive function of the evaluatee.

The present disclosure may be implemented not only by the cognitive function evaluation device and the cognitive function evaluation system, but by a program containing, as steps, the processing performed by the constituent elements of the cognitive function evaluation device and the cognitive function evaluation system. The present disclosure may also be implemented by a computer-readable recording medium storing the program, for example, a recording medium such as a flexible disk, a hard disk, a CD-ROM, an MO, a DVD, a DVD-ROM, a DVD-RAM, a Blu-ray Disk (registered trademark, BD), or a semiconductor memory. The program may be distributed via a communication channel such as internet.

The general and specific aspects described above may be implemented by a system, a device, an integrated circuit, a computer program, or a computer-readable recording medium, or any combination of systems, device, integrated circuits, computer programs, and computer-readable recording media. For example, the constituent elements of the cognitive function evaluation device are not necessarily included in a housing, buy may be arranged in different places and connected with various data transfer available.

The present disclosure includes other embodiments, such as those obtained by variously modifying the embodiment as conceived by those skilled in the art or those achieved by freely combining the constituent elements and functions in the embodiment without departing from the scope and spirit of the present disclosure.

The invention claimed is:

1. A cognitive function evaluation system, comprising:
a display device configured to display an image that indicates sentence data indicating a sentence to be uttered by an evaluatee, wherein the sentence to be uttered by the evaluatee is a sentence containing five or more characters, each character consisting of a stop consonant and a subsequent vowel;
a microphone configured to obtain utterance data indicating a voice of the evaluatee uttering the sentence as instructed by the image displayed by the display device;
computer configured to calculate, from the utterance data obtained by the microphone, a feature based on the utterance data, wherein the computer is further configured to compare the calculated feature to reference data indicating a relationship between voice data indicating a voice of a person and a cognitive function of the person to evaluate the cognitive function of the evaluatee; and
the display device is configured to output the sentence to be uttered by the evaluatee and output a result of evaluation by the computer, wherein
the sentence contains a character string of consecutive syllables, each including a vowel, and
wherein the sentence further contains at least three syllables, each including a vowel different from vowels of other syllables,
the computer is configured to calculate, as the feature, at least one of amounts of changes in a first formant frequency and a second formant frequency of a vowel, a number of times required for the changes in the first formant frequency and the second formant frequency of the vowel, or rates of changes that are ratios of the amounts of changes to the number of times required, and
further wherein computer calculates, as the feature, at least one of a shape or an area of a polygon defined by plotting a ratio of a second formant frequency to a first formant frequency calculated from the vowel of each of the at least three syllables in a coordinate space defined by the second formant frequency of the vowel with respect to the first formant frequency of the vowel; and
the display device further outputs an instruction for causing the evaluatee to utter the sentence a plurality of times,
the computer is further configured to calculate, as the feature, an amount of change in reading time calculated from reading times obtained for the plurality of times the evaluatee uttered the sentence, and further wherein the computer is configured to identify the vowel in the voice data and calculate the feature based on a formant obtained from a spectrum of the vowel identified; and
the computer further configured to evaluate that the cognitive function of the evaluatee decreases as a variation in the formant increases.

2. The cognitive function evaluation system of claim 1, wherein
the sentence contains a character string of at least one of consecutive syllables, each consisting of a consonant and a vowel subsequent to the consonant, or consecutive syllables, each consisting of a vowel only.

3. The cognitive function evaluation system of claim 1, wherein
the sentence contains at least one of character strings of "Kitakaze to taiyo ga deteimasu", "Tankenka wa bouken ga daisuki desu", or "Kita kara kita kata tatakiki".

4. The cognitive function evaluation system of claim 1, wherein
the sentence contains a plurality of syllables, each including a vowel, and
the calculation unit calculates, as the feature, at least one of variations in a first formant frequency of the vowel, a second formant frequency of the vowel, or a ratio of the second formant frequency of the vowel to the first formant frequency of the vowel.

5. The cognitive function evaluation system of claim 1, wherein
the sentence contains a syllable including a consonant and a vowel subsequent to the consonant, and
the calculation unit calculates, as the feature, a difference in a voice pressure between the consonant and the vowel.

6. The cognitive function evaluation system of claim 1, wherein
the calculation unit calculates, as the feature, a time required for the evaluatee to utter the sentence.

7. The cognitive function evaluation system according to claim 1, further comprising:
a storage unit configured to store the reference data.

8. The cognitive function evaluation system of claim 1, comprising:
a voice collection device that detects the voice of the evaluatee; and
the display device that displays the sentence and the result of the evaluation by the computer.

9. A cognitive function evaluation method executed by a computer, the cognitive function evaluation method comprising:
displaying, by a display device, an image that indicates sentence data indicating a sentence to be uttered by an evaluatee and further outputting an instruction for causing the evaluatee to utter the sentence a plurality of times, the sentence to be uttered by the evaluate is a sentence containing five or more characters each consisting of a stop consonant and a subsequent vowel;
wherein the sentence further contains at least three syllables, each including a vowel different from vowels of other syllables,
obtaining utterance data captured using a microphone indicating a voice of the evaluatee uttering the sentence;
calculating, from the utterance data, a feature based on the utterance data and calculating, as the feature, an amount of change in reading time calculated from reading times obtained for the plurality of times the evaluatee uttered the sentence;
evaluating, by the computer, a cognitive function of the evaluatee by comparing the feature calculated in the calculating to reference data indicating a relationship between voice data indicating a voice of a person and a cognitive function of the person; and
outputting a result of the evaluating wherein the sentence contains a character string of consecutive syllables, each including a vowel, and
calculating, by the computer,
at least one of amounts of changes in a first formant frequency and a second formant frequency of a vowel, a number of times required for the changes in the first formant frequency and the second formant frequency of the vowel, or rates of changes that are ratios of the amounts of changes to the number of times required, and further
wherein the computer is further configured to identify the vowel in the voice data and calculate the feature based on a formant obtained from a spectrum of the vowel identified; and
the computer further calculates, as the feature, at least one of a shape or an area of a polygon defined by plotting a ratio of a second formant frequency to a first formant frequency calculated from the vowel of each of the at least three syllables in a coordinate space defined by the second formant frequency of the vowel with respect to the first formant frequency of the vowel; and
the computer is further configured to evaluate that the cognitive function of the evaluatee decreases as a variation in the formant increases.

10. A non-transitory computer-readable storage medium storing program for causing a computer to execute a cognitive function evaluation method, the cognitive function evaluation method comprising:
displaying, by a display device, an image that indicates sentence data indicating a sentence to be uttered by an evaluatee and further outputting an instruction for causing the evaluatee to utter the sentence a plurality of times, the sentence to be uttered by the evaluate is a sentence containing five or more characters each consisting of a stop consonant and a subsequent vowel;
wherein the sentence further contains at least two consecutive syllables, each including a vowel different from vowels of another syllables,
obtaining utterance data captured using a microphone indicating a voice of the evaluatee uttering the sentence;
calculating, by the computer, from the utterance data, a feature based on the utterance data and calculating, as the feature, an amount of change in reading time calculated from reading times obtained for the plurality of times the evaluatee uttered the sentence;
evaluating, by executing the computer, a cognitive function of the evaluatee by comparing the feature calculated in the calculating to reference data indicating a relationship between voice data indicating a voice of a person and a cognitive function of the person; and
outputting a result of the evaluating wherein the sentence contains a character string of consecutive syllables, and each including a vowel,
calculating, by executing the computer, at least one of amounts of changes in a first formant frequency and a second formant frequency of a vowel, a number of times required for the changes in the first formant frequency and the second formant frequency of the vowel, or rates of changes that are ratios of amounts of changes to the number of times required, and
further wherein computer calculates, as the feature, a positional relationship when plotting a ratio of a second formant frequency to a first formant frequency calculated from the vowel of each of the at least two consecutive syllables in a coordinate space defined by the second formant frequency of the vowel with respect to the first formant frequency of the vowel; and
further wherein the computer is further configured to identify the vowel in the voice data and calculate the feature based on a formant obtained from a spectrum of the vowel identified; and
the computer is further configured to evaluate that the cognitive function of the evaluatee as a variation in the formant increases.

11. A cognitive function evaluation system, comprising:
a display device configured to display an image that indicates sentence data indicating a sentence to be uttered by an evaluatee, wherein the sentence to be uttered by the evaluatee is a sentence containing five or more characters, each character consisting of a stop consonant and a subsequent vowel;
a microphone configured to obtain utterance data indicating a voice of the evaluatee uttering the sentence as instructed by the image displayed by the display device;
computer configured to calculate, from the utterance data obtained by the microphone, a feature based on the utterance data, wherein the computer is further configured to compare the calculated feature to reference data indicating a relationship between voice data indicating a voice of a person and a cognitive function of the person to evaluate the cognitive function of the evaluatee; and the display device is configured to output the sentence to be uttered by the evaluatee and output a result of evaluation by the computer, wherein the sentence contains a character string of consecutive syllables, each including a vowel, and wherein the sentence further contains at least two consecutive syllables, each including a vowel different from vowels of another syllables, the computer is configured to calculate, as the feature, at least one of amounts of changes in a first formant frequency and a second formant frequency of a vowel, a number of times required for the changes in the first formant frequency and the second formant frequency of the vowel, or rates of changes that are ratios of the amounts of changes to the number of times required, and further wherein computer calculates, as the feature, a positional relationship when plotting a ratio of a second formant frequency to a first formant frequency calculated from the vowel of each of the at least two consecutive syllables in a coordinate space defined by the second formant frequency of the vowel with respect to the first formant frequency of the vowel; and the display device further outputs an instruction for causing the evaluatee to utter the sentence a plurality of times, the computer is further configured to calculate, as the feature, an amount of change in reading time calculated from reading times obtained for the plurality of times the evaluatee uttered the sentence, and further wherein the computer is configured to identify the vowel in the voice data and calculate the feature based on a formant obtained from a spectrum of the vowel identified; and the computer further configured to evaluate that the cognitive function of the evaluatee decreases as a variation in the formant increases.

12. A cognitive function evaluation method executed by a computer, the cognitive function evaluation method comprising:

displaying, by a display device, an image that indicates sentence data indicating a sentence to be uttered by an evaluatee and further outputting an instruction for causing the evaluatee to utter the sentence a plurality of times, the sentence to be uttered by the evaluate is a sentence containing five or more characters each consisting of a stop consonant and a subsequent vowel;

wherein the sentence further contains at least two consecutive syllables, each including a vowel different from vowels of another syllables, obtaining utterance data captured using a microphone indicating a voice of the evaluatee uttering the sentence;

calculating, from the utterance data, a feature based on the utterance data and calculating, as the feature, an amount of change in reading time calculated from reading times obtained for the plurality of times the evaluatee uttered the sentence;

evaluating, by the computer, a cognitive function of the evaluatee by comparing the feature calculated in the calculating to reference data indicating a relationship between voice data indicating a voice of a person and a cognitive function of the person; and outputting a result of the evaluating wherein the sentence contains a character string of consecutive syllables, each including a vowel, and calculating, by the computer, at least one of amounts of changes in a first formant frequency and a second formant frequency of a vowel, a number of times required for the changes in the first formant frequency and the second formant frequency of the vowel, or rates of changes that are ratios of the amounts of changes to the number of times required, and further wherein the computer is further configured to identify the vowel in the voice data and calculate the feature based on a formant obtained from a spectrum of the vowel identified; and the computer further calculates, as the feature, a positional relationship when plotting a ratio of a second formant frequency to a first formant frequency calculated from the vowel of each of the at least two consecutive syllables in a coordinate space defined by the second formant frequency of the vowel with respect to the first formant frequency of the vowel; and the computer is further configured to evaluate that the cognitive function of the evaluatee decreases as a variation in the formant increases.

13. A non-transitory computer-readable storage medium storing program for causing a computer to execute a cognitive function evaluation method, the cognitive function evaluation method comprising:

displaying, by a display device, an image that indicates sentence data indicating a sentence to be uttered by an evaluatee and further outputting an instruction for causing the evaluatee to utter the sentence a plurality of times, the sentence to be uttered by the evaluate is a sentence containing five or more characters each consisting of a stop consonant and a subsequent vowel;

wherein the sentence further contains at least two consecutive syllables, each including a vowel different from vowels of another syllables, obtaining utterance data captured using a microphone indicating a voice of the evaluatee uttering the sentence;

calculating, by the computer, from the utterance data, a feature based on the utterance data and calculating, as the feature, an amount of change in reading time calculated from reading times obtained for the plurality of times the evaluatee uttered the sentence;

evaluating, by executing the computer, a cognitive function of the evaluatee by comparing the feature calculated in the calculating to reference data indicating a relationship between voice data indicating a voice of a person and a cognitive function of the person; and outputting a result of the evaluating wherein the sentence contains a character string of consecutive syllables, and each including a vowel, calculating, by executing the computer, at least one of amounts of changes in a first formant frequency and a second formant frequency of a vowel, a number of times required for the changes in the first formant frequency and the second formant frequency of the vowel, or rates of changes that are ratios of amounts of changes to the number of times required, and the computer further calculates, as the feature, a positional relationship when plotting a ratio of a second formant frequency to a first formant frequency calculated from the vowel of each of the at least two consecutive syllables in a coordinate space defined by the second formant frequency of the vowel with respect to the first formant frequency of the vowel; and further wherein the computer is further configured to identify the vowel in the voice data and calculate the feature based on a formant obtained from a spectrum of the vowel identified; and the computer is further configured to evaluate that the cognitive function of the evaluatee as a variation in the formant increases.

* * * * *